United States Patent
Kuzma et al.

(10) Patent No.: US 6,259,951 B1
(45) Date of Patent: Jul. 10, 2001

(54) IMPLANTABLE COCHLEAR STIMULATOR SYSTEM INCORPORATING COMBINATION ELECTRODE/TRANSDUCER

(75) Inventors: Janusz A. Kuzma, Englewood, CO (US); William Vanbrooks Harrison, Valencia, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/569,696

(22) Filed: May 12, 2000

Related U.S. Application Data

(60) Provisional application No. 60/134,289, filed on May 14, 1999, provisional application No. 60/134,290, filed on May 14, 1999, and provisional application No. 60/155,840, filed on Sep. 24, 1999.

(51) Int. Cl.[7] ........................................ A61N 1/00
(52) U.S. Cl. ............................... 607/57; 607/137; 600/25
(58) Field of Search .......................... 607/55–57, 137; 600/25, 379, 559; 623/10; 381/68

(56) References Cited

U.S. PATENT DOCUMENTS

| | | | |
|---|---|---|---|
| 3,764,478 | 10/1973 | Branch et al. | 179/107 |
| 5,176,620 | 1/1993 | Gilman | 600/25 |
| 5,318,502 | 6/1994 | Gilman | 600/25 |
| 5,411,467 | 5/1995 | Hortmann et al. | 600/25 |
| 5,603,726 | 2/1997 | Schulman et al. | 607/57 |
| 5,776,172 | 7/1998 | Schulman et al. | 607/56 |
| 5,776,179 | 7/1998 | Ren et al. | 607/137 |
| 5,782,744 | 7/1998 | Money | 600/25 |
| 5,800,475 | 9/1998 | Jules | 607/57 |
| 5,906,635 | 5/1999 | Maniglia | 607/57 |
| 5,935,166 | 8/1999 | Kennedy | 623/10 |
| 5,999,856 | 12/1999 | Kennedy | 607/57 |
| 6,010,532 | 1/2000 | Kroll et al. | 623/10 |

FOREIGN PATENT DOCUMENTS 9718689    5/1997  (WO).

*Primary Examiner*—Jeffrey R. Jastrzab
(74) *Attorney, Agent, or Firm*—Bryant R. Gold

(57) ABSTRACT

A hearing aid system provides acoustic modulation of the fluid within the cochlea of the inner ear corresponding to a first frequency range of sensed acoustic signals, e.g., lower-to-middle frequencies of the audible range, and electrical stimulation of the cochlea corresponding to a second frequency range, e.g., high frequencies of the audible range. In a preferred implementation, a short electrode/transducer array is provided for use with the hearing system. Such array is adapted to be inserted into the basal region of the scala tympani of the cochlea. The electrode/transducer array includes a plurality of spaced-apart electrode contacts through which electrical stimulation is provided to stimulate ganglion cells located in the basal region of the cochlea, which cells are responsible for perceiving the higher frequencies of the acoustic energy. The electrode/transducer further includes an acoustic modulator as an integral part thereof, in fluid communication with an acoustic transducer, through which acoustic modulation may be coupled to the fluid within the cochlea, thereby allowing normal hearing processes to occur in the cochlea. In the preferred implementation, the lower frequencies of sensed acoustic energy are processed to provide modulation of the acoustic modulator. An implantable cochlear stimulator (ICS), including the acoustic transducer and coil, and implantable speech processor (ISP), including an implantable microphone, are used with the system. In an alternative embodiment, the acoustic modulator within the electrode/transducer array is used as a sensor, to sense fluid modulation within the cochlea resulting from a functioning middle ear, and the acoustic transducer converts such sensed fluid modulation to electrical signals, thereby providing the function of an microphone implanted in the cochlea.

18 Claims, 3 Drawing Sheets

IMPLANTABLE COCHLEAR STIMULATOR SYSTEM INCORPORATING COMBINATION ELECTRODE/TRANSDUCER

This application claims the benefit of U.S. Provisional Patent Applications Ser. No. 60/134,289, filed May 14, 1999; Ser. No. 60/134,290, filed May 14, 1999; and Ser. No. 60/155,840, filed Sep. 24, 1999, each application of which is incorporated herein by reference.

BACKGROUND OF THE INVENTION

The present invention relates to hearing aid systems, and more particularly to a hearing aid system that combines an implantable cochlear stimulator system, including a cochlear electrode array, with a cochlear acoustic transducer, coupled to an implantable or other microphone. Such system relies primarily on the cochlear stimulator portion for sensing high frequency sounds, and relies primarily on normal hearing processes, augmented by the cochlear acoustic transducer, for sensing lower frequency sounds. Such hearing aid system utilizes a short cochlear electrode array, e.g., of the type described in applicant's copending patent application, Ser. No. 60/134,290, filed May 14, 1999, entitled "Electrode Array for Hybrid Cochlear Stimulator", into which an acoustic transducer has been integrated.

Hearing loss is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

Sensorineural hearing loss, on the other hand, results due to the absence or the destruction of the hair cells in the cochlea which are needed to transduce acoustic signals into auditory nerve impulses. Persons who suffer from sensorineural hearing loss are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea by presenting electrical stimuli directly to the ganglia of the auditory nerve located adjacent the modiolar wall of the cochlea. When triggered, the ganglia, also referred to as ganglion cells, send nerve impulses to the brain via the auditory nerve, leading to the perception of sound in the brain, and an at least partial restoration of hearing function. The common denominator in these cochlear prosthesis systems has been the implantation into the cochlea of electrodes which are responsive to a suitable external source of electrical stimuli and which are intended to transmit those stimuli to the ganglion cells, and thereby to the auditory nerve fibers.

As people age, they frequently experience progressive hearing loss. Usually this loss is more prevalent and more severe at higher frequencies. Thus, it is estimated that a large segment of the hearing-impaired population exhibit sensorineural hearing loss relative to high frequency sounds, but maintain the ability to transduce middle-to-lower frequency sounds through functioning hair cells.

The usual method to restore this high frequency hearing loss is by using a hearing aid that increases the amplitude of the acoustic energy applied to the tympani membrane. Although effective, this approach does not provide the same level of restoration to high frequencies as it does to lower frequencies. Also, the increase in acoustic amplitudes used in this method can ofttimes further degrade residual hearing, resulting in a further decrease in the ability to hear the higher frequencies.

It is thus evident that there is a need for a "hybrid" cochlear stimulation system that electrically stimulates only the ganglion cells responsible for sensing higher frequency sounds, while allowing or permitting the normal hearing process (e.g., activation of hair cells through wave motion of the fluid within the cochlea) to function for the purpose of sensing lower-to-middle frequency sounds.

A cochlear prosthesis operates by direct electrical stimulation of the auditory nerve cells, bypassing the defective cochlear hair cells that normally transduce acoustic energy into electrical activity in such nerve cells. Because the ganglion cells responsible for sensing higher frequency sounds are all generally located in or near the basal end of the cochlea (the end of the cochlea nearest the round window), a hybrid cochlear stimulation system thus requires an electrode array that can be inserted within the cochlea a sufficient depth to be near such cells, but which also does not block or significantly interfere with the normal functioning of the cochlea for hair cells located deeper within the cochlea. Thus, there is a need for such an electrode array that may be used with an implantable cochlear stimulator hearing system.

Because any electrode array inserted into the cochlea is likely to block the cochlea to a certain extent, and thereby interfere (even if only minimally) with the normal functioning of the hair cells located deeper within the cochlea, there is also a need to augment, or to restore, the normal hearing pathways (i.e., the fluid path) to those hair cells located deep within the cochlea.

SUMMARY OF THE INVENTION

The present invention addresses the above and other needs by providing a cochlear stimulation hearing system that also includes an acoustic modulator to acoustically modulate the fluid within the cochlea for acoustic information corresponding to a first frequency range, e.g., lower-to-middle frequencies of the audible range. Cochlear electrical stimulation is provided for acoustic information corresponding to a second frequency range, e.g., high frequencies of the audible range. A short electrode/transducer array is used with the hearing system. Such electrode/transducer array is adapted to be inserted into the basal region of the scala tympani of the cochlea. The electrode/transducer array includes a plurality of spaced-apart electrode contacts through which electrical stimulation is provided to stimulate ganglion cells located in the basal region of the cochlea. Such cells are responsible for perceiving the higher frequencies of the acoustic energy. The electrode/transducer array further includes an acoustic modulator as an integral part thereof. This acoustic modulator is in fluid communication with an acoustic transducer, not included as part of the array. The acoustic modulator applies acoustic modulation to the fluid within the cochlea corresponding to the lower frequencies of sensed acoustic energy. An implantable cochlear stimulator (ICS), which includes the acoustic transducer as part thereof, and an implantable speech processor (ISP), which may also include an implantable microphone as part thereof, also form elements of the hearing system. In an alternative embodiment, the acoustic modulator within the electrode/transducer array is used as a sensor, to sense fluid modulation within the cochlea resulting from a functioning middle ear, and the acoustic transducer converts such sensed fluid modulation to electrical signals, thereby providing the function of a microphone implanted in the cochlea.

Thus, the present invention provides an implantable cochlear stimulator system that relies primarily on the cochlear stimulator portion of the system for perceiving high frequency sounds, and provides an implantable acoustic modulator, integral with an electrode used as part of the cochlear stimulator, to acoustically vibrate fluid within the cochlea, thereby augmenting the normal hearing processes, i.e., fluid activation of hair cells located deeper within the cochlea, so as to better perceive lower frequency sounds.

In a preferred embodiment, the cochlear stimulating system of the present invention comprises: (1) an implantable speech processor (ISP); (2) an implantable cochlear stimulator (ICS); and (3) an electrode/transducer.

The implantable speech processor (ISP) is electrically connected to the implantable stimulator by way of an implantable cable or lead, typically having five conductors therein. The implantable speech processor includes: (1) an implantable microphone; (2) electrical processing circuitry that coverts acoustic signals picked up or sensed by the microphone to appropriate control signals for use by the implantable stimulator; (3) a rechargeable battery or other power source, e.g., a super capacitor; and (4) a connector that allows the cable or lead going to the implantable stimulator to be detached from the implantable speech processor.

The implantable cochlear stimulator (ICS) has two leads permanently attached thereto: (1) a first lead that connects to the implantable speech processor; and (2) a second lead that is connected to the electrode/transducer. The ICS includes electrical circuitry that responds to a first set of control signals received from the speech processor and provides electrical stimulation pulses to electrode contacts located on the electrode/transducer. It is the electrical current associated with these electrical stimulation pulses that flows through the modiolar wall and stimulates the ganglion cells located near the basal region of the cochlea. The stimulation of these ganglion cells, in turn, is what provides a high frequency hearing sensation to the user.

The electrode/transducer is adapted for insertion into the basal end of a human cochlea, typically inside of the scala tympani. The electrode/transducer comprises an elongate carrier of from 6–10 mm in length and approximately 2 mm in diameter. Such electrode/transducer is located at a distal end of the second lead. A plurality of spaced-apart electrode contacts are carried on or exposed at the surface of the elongate carrier. Inside the elongate carrier, or attached thereto, is an acoustic modulator, e.g., a balloon compartment, filled with a suitable fluid, e.g., a saline liquid. The electrode contacts are each electrically connected to stimulating electrical circuitry housed within the ICS by way of the second lead. The second lead, which is an implantable lead, includes individual wires, at least one wire for each electrode contact, that are bundled, embedded or otherwise carried within it. The acoustic modulator inside of the electrode/transducer is in fluid communication with an acoustic modulator, typically housed within the ICS, by way of an acoustic tunnel that passes through the second lead.

The electrode contacts of the electrode/transducer are interspersed along its length. Typically, 3 or 4 electrode contacts are used. It is through these electrode contacts that electrical stimulation is applied to stimulate the ganglion cells located near the basal end of the cochlea. Advantageously, electrical stimulation of the ganglion cells near the basal end of the cochlea provides the user of the system with the ability to sense high frequency sounds.

In one mode of operation, the acoustic modulator inside of the electrode/transducer, when modulated with acoustic information, sets up pressure waves within the fluid inside of the cochlea. These pressure waves traverse a normal course deeper into the cochlea, and thereby stimulate hair cells located deeper in the cochlea. In other words, these waves or vibrations set up by the acoustic modulator reestablish or augment fluid motion within the cochlea to better activate the hair cells located deeper within the cochlea, thereby enhancing the user's ability to sense lower frequency sounds. The stimulation of these deep-in-the-cochlea hair cells, in turn, provides the user of the system with the ability to better perceive middle-to-lower frequency sounds.

Thus, it is seen that, in combination, electrical stimulation of the ganglion cells located near the basal end of the cochlea, coupled with modulation of the acoustic modulator (also positioned near the basal end of the cochlea) provide the user of the hearing system with the ability to better perceive sound of high, middle, and low frequencies.

Hence, it is seen that one advantage provided by the invention is that high, middle and low frequency sound perception is provided and/or enhanced through use of a single short electrode/transducer array that need only be inserted into the basal end of the cochlea. Unlike prior art cochlea stimulation systems, it is therefore not necessary to insert an electrode array deep into the cochlea.

Another advantage of the invention is that the hearing system is fully implantable. That is, all components used with the system during its normal operation may be permanently implanted. The only external components required with the system, for use at times other than normal operation, i.e., during a programming and/or recharging mode, are: (1) a programmer (used by the physician and/or audiologist) to set up or adjust the operating parameters of the system, and (2) a recharging unit (used at regular intervals of, e.g., once a day or once every other day) to recharge the battery (or other power source) within the implantable speech processor.

In an alternate mode of operation, the acoustic modulator within the electrode/transducer array may be used as an implanted cochlear microphone. That is, assuming functionality of the middle ear, external audio sounds set up or establish fluid waves or vibrations inside the cochlea. Unfortunately, for patients suffering from sensorial hearing loss, such vibrations are not sensed through the hair cells. However, such vibrations may be sensed through the acoustic modulator provided by the present invention, and transmitted, through the fluid communication channel, to the acoustic transducer. The acoustic transducer, in turn, converts the sensed vibrations to an electrical signal, which electrical signal may then be used as a microphone signal, processed by the speech processor, and acted upon by the ISP and ICS in order to stimulate ganglion cells within the cochlea.

In operation, the implantable speech processor (ISP) includes a front-end amplifier and processor and spectral decomposition filters. Such circuitry may be the same for both acoustic boost and neural stimulation applications. The frequencies are separated and sent to circuits that either convert the signals into mechanical vibrations (e.g., fluid vibrations) to provide or boost low-to-middle frequency acoustic energy, or into high frequency energy that is further divided and converted to stimulation pulses that are applied directly to the neurons located in the basal region of the cochlea through the electrode contacts of the electrode/transducer. As desired, a smoothing circuit may be provided to allow a smooth, seamless transition from the acoustic enhancement provided for low-to-middle frequencies and the neural stimulation provided for the high frequencies.

It is a feature of the invention that the microphone used therewith, in a preferred embodiment, is an implantable microphone, thereby allowing the entire system to be fully implantable.

It is another feature of the invention that an acoustic modulator be formed as an integral part of an electrode array adapted for insertion into the cochlea, thereby forming an electrode/transducer array. In a preferred implementation, such acoustic modulator comprises a balloon compartment formed within the carrier of the electrode array, where such balloon compartment is in fluid communication with an acoustic transducer located in a remote location, e.g., within an implantable cochlear stimulator, not inside the cochlea.

It is an additional feature of the invention that a storage reservoir, chamber or compartment also be provided in the electrode/transducer array wherein steroids or drugs may be held or cached and then time-released over days, weeks, months, or years for the purpose of inhibiting tissue growth around the electrode/transducer, or otherwise treating the tissue in the vicinity of the electrode/transducer in a prescribed manner.

It is a further feature of the hearing system of the invention that it may also be used to suppress tinnitus (which is a buzzing, or ringing, sound in the ear) by delivering special pulse sequences on some of the electrodes located in the basal region of the cochlea, at the same time that acoustic enhancement is provided in the low frequency range.

Advantageously, the hearing system of the present invention may be used for several applications. Such applications include, but are not limited to:

(a) high frequency neural stimulation combined with residual low frequency hearing;

(b) high frequency neural stimulation signal enhancement combined with low frequency acoustic signal enhancement;

(c) tinnitus suppression;

(d) tinnitus suppression combined with low frequency acoustic signal enhancement;

(e) high frequency neural stimulation signal enhancement, acoustic signal enhancement, and tinnitus suppression stimulation; or (f) tinnitus suppression combined with cochlear neural stimulation.

It is thus an object of the present invention to provide a cochlear stimulation system that restores hearing function over a wide frequency band, e.g., from low frequencies to high frequencies.

It is another object of the invention to provide a cochlear electrode array that has an acoustic modulator formed as an integral part thereof, which acoustic modulator may be used to enhance audibly-excited fluid motion within the cochlea, thereby boosting or augmenting the capacity of hair cells in the cochlea to be triggered and perceive such motion as sound, or alternatively to sense audibly-generated fluid motion within the cochlea, thereby providing an implanted cochlear microphone.

It is a further object of the invention to provide such a cochlear stimulation system wherein all of the components of the system, except those used occasionally for programming and/or recharging, may be implanted, thereby providing a fully implantable cochlear stimulation system during normal operation.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components or elements throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
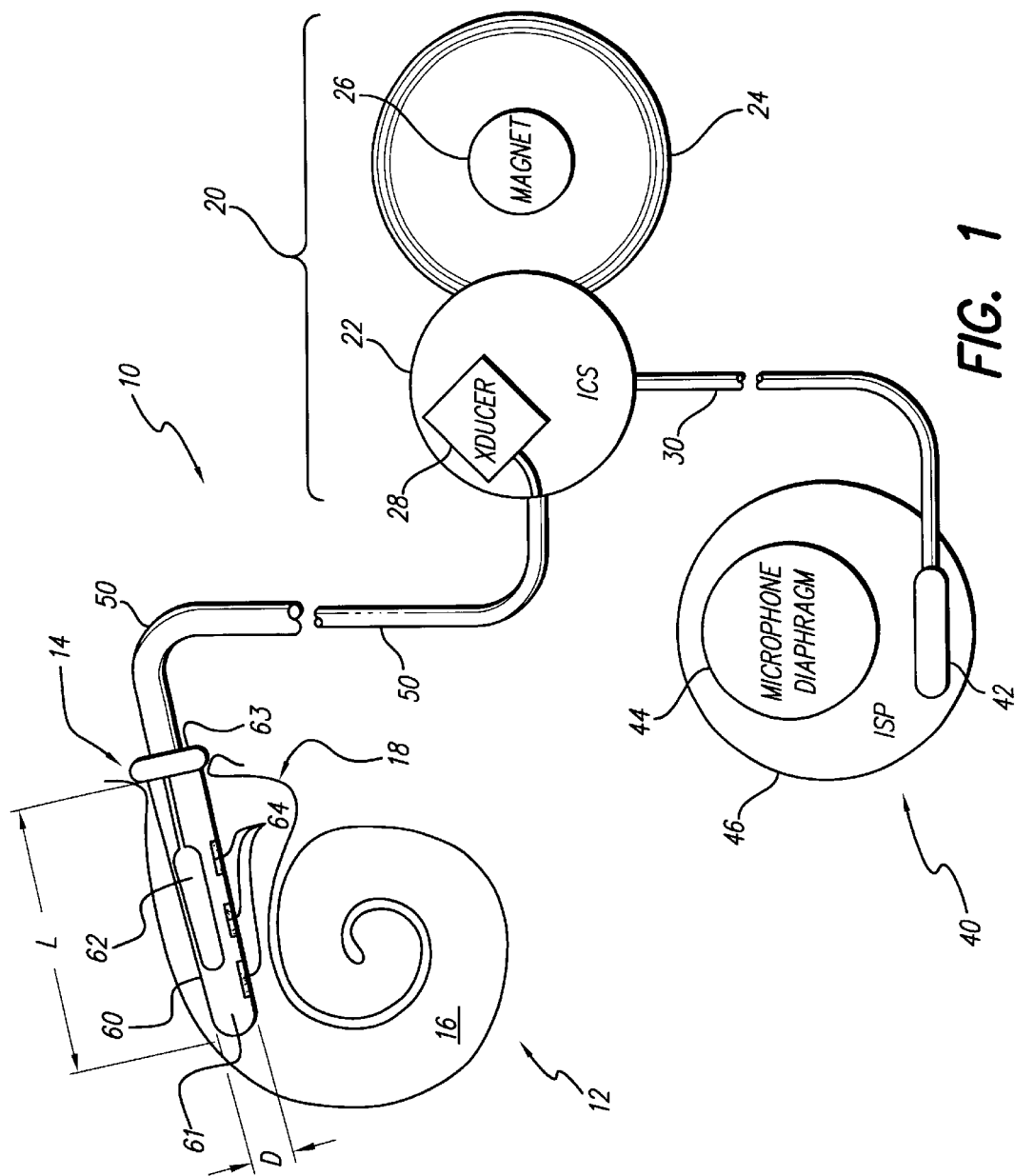
FIG. 1 is a block diagram of a preferred embodiment of the hearing system of the present invention.

Turning first to FIG. 1, a block diagram of a hearing system 10 made in accordance with the present invention is illustrated. As seen in FIG. 1, the system 10 includes three main components: an implantable speech processor (ISP) 40, an implantable cochlear stimulator (ICS) 20, and an electrode/transducer array 60. The ICS 20 is electrically connected to the ISP 40 by way of a first flexible cable 30. The first cable 30 is permanently attached at one end to the ICS 20, and is detachably connected at its other end to the ISP 40 by way of a connector 42 which is built-in to the case of the ISP 40. The electrode/transducer array 60 is connected to the ICS 20 by way of a second flexible cable 50. The second cable 50 is permanently attached at its distal end to the array 60 and is permanently attached at is proximal end to the ICS 20.

The electrode/transducer array 60 is formed on a flexible carrier body 61 made of a suitable non-conductive biocompatible material, such as silicone rubber, or silastic, or an equivalent material. The electrode/transducer array 60 has a plurality of spaced-apart exposed electrode contacts 64 thereon. In general, there may be as few as two or as many as eight electrode contacts 64 carried by the array 60. In one embodiment, the number of electrode contacts 64 is no more than five, and is typically three. Each electrode contact 64 is in electrical contact with pulse generation circuitry within the ICS 20 by way of respective wires 69 that pass through the flexible lead 50. Also, included within the body of the flexible carrier 61 is an acoustic modulator 62. The acoustic modulator 62, in a preferred embodiment, comprises a balloon compartment. The balloon compartment, which may hereafter be referred to as the"balloon compartment 62", or simply the "compartment 62", as is explained more fully below, functions as an acoustic modulator and is in fluid communication with an acoustic transducer 28. Typically, the acoustic transducer 28 is housed within the ICS 20. However, depending upon the size and nature of the transducer 28, it may also be located within the lead 50, or even at a proximal tip of the electrode/transducer 60 (e.g., at a tip portion that is not inserted into the cochlea, but resides just outside of the cochlea).

The fluid communication between the acoustic modulator, e.g., balloon compartment, 62 and the acoustic transducer 28 is realized by a tunnel 65 (see FIG. 2), or lumen, that passes through the lead 50. The balloon compartment 62, and the tunnel 65, and a fluid compartment portion 25 of the acoustic transducer 28 are filled with a suitable acoustic transferring (or acoustically conductive) medium 67. In a preferred embodiment, the transferring medium 67 comprises a suitable fluid, e.g., a saline solution (liquid). It is to be understood, however, that the term "fluid", as used herein, is not necessarily restricted to a liquid, but may comprise any medium, whether in a gas, fluid, or solid state, that is an effective conductor, or transferring medium, of acoustic energy.

Referring again to FIG. 1, the ISP 40 includes processing circuitry for receiving a microphone signal(s), representative of sensed acoustic sound waves, and converting such microphone signal(s) to appropriate stimulation control signals, in accordance with a selected speech processing strategy. All of the speech processing circuitry associated with the ISP 40 is housed within an hermetically-sealed ISP case 46. Electrical connection with such circuitry is established through a connector 42 that attaches to one end of the flexible cable 30. In a preferred implementation, the cable includes 5 conductors. Also included within the ISP case 46, in the preferred embodiment, is a rechargeable battery or equivalent replenishable power source.

As indicated in FIG. 1, the ISP case 46 also houses a microphone diaphragm 44. Such diaphragm 44 is coupled to a suitable transducer, e.g., a piezoelectric element, that converts mechanical stress or deflection of the diaphragm 44 to corresponding electrical signals. Hence, by implanting the ISP case 46 near the surface of the skin, with the microphone diaphragm 44 positioned closest to the skin, acoustic sound waves that impinge on the skin are coupled to the diaphragm 44 and cause it to deflect or move as a function of the acoustic waves, as in any microphone. Such deflection is then converted to an analog electrical signal which is used as an input signal for the ISP circuitry.

While the preferred embodiment of the invention uses the microphone diaphragm 44 and a corresponding transducer within the ISP case 46 as the source for the microphone signal(s) for the hearing system 10, it is to be understood that other microphones could also be used with the system 10, either instead of or in conjunction with, the microphone diaphragm 44. Such other microphones may comprise, e.g., an external (non-implanted) microphone, or an in-the-ear-canal microphone, that is in RF communication with circuitry within the ISP 40, or an in-the-cochlea microphone. Advantageously an in-the-cochlea microphone may be realized using the components of the hearing system 10 of the present invention, as described more fully below.

Still with reference to FIG. 1, the control signals generated by the ISP 40 are sent to the ICS 20 over the cable 30. The implantable stimulator 20, in turn, responds to the stimulation control signals in one of two ways. First, for those control signals that are indicative of a high frequency content of the sensed microphone signal(s), such signals cause electrical stimulation pulses to be generated which are applied to selected electrode contacts 64 of the electrode/transducer 60. These electrical stimulation pulses have an amplitude, pulse width, and pulse rate defined by a selected speech processing strategy and other parameters (e.g., the amplitude of the microphone signal(s)). Second, for those control signals that are indicative of a middle-to-lower frequency content of the sensed microphone signal(s), such signals are used to modulate the acoustic transducer 28. The information content of the control signals associated with middle-to-lower frequencies is thus transferred to the balloon compartment 62 within the electrode/transducer 60, where it is coupled to the fluid medium naturally present within the cochlea, and is thus transferred to hair cells throughout the cochlea, particularly those hair cells deeper within the cochlea.

Still with reference to FIG. 1, the ICS 20 includes a round, hermetically-sealed stimulator case 22 wherein the stimulator circuitry and acoustic transducer are housed. Both the cable 50, going to the electrode/transducer 60, and the cable 30, going to the implantable speech processor (ISP) 40 are permanently attached to the circuitry within the ICS 20 through appropriate feed-through connections that pass through the hermetically-sealed ICS case 22. Also connected to the ICS circuitry, through additional feed-through connections, is a coil 24. The coil 24 has a diameter approximately the same as, or somewhat larger than, the round ICS case 22. The coil 24 is adapted to be inductively coupled, or rf-coupled, with an external coil (not shown) during programming and recharging modes of operation. The coil 24 is preferably embedded within a soft silastic material which allows the coil to flex somewhat with respect to the round case 22 so that both may be readily implanted under the patients skin against a somewhat curving skull bone. Also embedded within such silastic material, in the center of the coil 24, is a permanent magnet 26. The permanent magnet 26 allows an external headpiece, housing an external coil, and also having a permanent magnet or equivalent element that is magnetically attracted to the implanted magnet 26, to be properly aligned with the coil 24 during a recharging and/or programming mode of operation.

As evident from FIG. 1 and the above description, the hearing system 10 made up of the implantable speech processor (ISP) 40, implantable cochlear stimulator (ICS) 20, and electrode/transducer array 60 cooperate to comprise a fully implantable hearing system. Additional details associated with such system, including details associated with the operation and design of the ISP 40 and the ICS 20 may be the same as, or similar to, the information disclosed in Applicant's copending patent application, "Fully Implantable Cochlear Implant System", Ser. No. 09/404,966, filed Sep. 24, 1999, which application is incorporated herein by reference. The fully implantable cochlear implant system disclosed in the referenced patent application utilizes a conventional cochlear electrode array, rather than the electrode/transducer array 60 and associated acoustic transducer 28, of the type disclosed herein. Other than those differences, the system disclosed in the referenced patent application is very similar to the system 10 disclosed herein.

Because the system 10 relies upon normal operation of the cochlea to sense middle-to-low frequencies, it is preferable, as shown in FIG. 1, that the round window 18 of the cochlea 12 be left intact. (In a cochlear implant system utilizing a conventional electrode array that is inserted deep into the cochlea, it is common to insert the electrode array through the round window, thereby effectively eliminating any possibility that the round window could still perform its intended function. The intended function of the round window is to seal fluids within the cochlea, as well as to set up fluid vibrations inside the cochlea based on mechanical movement of the round window induced by oscillations of the ossicle chain in the middle ear.) For that reason, the electrode/transducer 60 is preferably inserted into the cochlea by way of a cochleostomy 14. Such cochleostomy typically involves drilling a hole to the side of the round window 18. Then, once the electrode/transducer 60 has been inserted into the fluid-filled scala tympani 16 of the cochlea 12, vibrations established in the balloon compartment 62 of the electrode/transducer 60 are coupled to the fluid inside the scala tympani 16 (one of the three ducts within the cochlea 12), and these vibrations serve to stimulate the functional hair cells located deeper within the scala tympani responsible for perceiving middle-to-lower frequencies. At the same time, electrical stimulation of the electrode contacts 64 with appropriate electrical current stimulation pulses, causes the ganglion cells near the electrode contacts to be stimulated, which ganglion cells, located near the basal end of the cochlea, are primarily responsible for perceiving higher frequency sounds. In this manner, the user is able to perceive a full range of sounds, from low frequencies to high frequencies.

Another reason for leaving the round window intact, in accordance with another embodiment of the invention, is so that the round window can perform its intended function of vibrating, in response to vibrations passed through the ossicle chain of the middle ear, to thereby set up vibrations or waves within the fluid inside the cochlea. In a person having normal hearing, it is these vibrations or waves established in the fluid-filled cochlea that trigger the hair cells that line the cochlea, which in turn activate the ganglion cells, thereby providing the sensation of hearing. In a deaf and/or older person, however, at least some of these hair cells may not function. Thus, even though the middle ear is functioning, and the round window is coupling sound vibrations into the fluid within the cochlea, such vibrations or waves may not all be perceived as sound due to malfunctioning, diseased or missing hair cells. In particular, it is common in older persons, for example, for at least the hair cells near the basal end of the cochlea to stop functioning, thereby making it difficult for the person with such condition to perceive high frequency sounds. For such persons, the electrode/transducer 60 of the present invention may advantageously be used as an implantable cochlear microphone. That is, the vibrations or waves established within the fluid-filled cochlea by vibration of the round window membrane or other sound waves received at the inner ear, normally caused by sound waves passing through the functioning outer and middle ear components (but which sound waves may also arrive at the middle ear through other paths, e.g., bone conduction), are coupled to the fluid within the fluid-filled balloon compartment 62. These vibrations, in turn, may then be sensed at the acoustic transducer 28 and converted to electrical signals. These electrical signals, or microphone signals, are then amplified, as required, and passed on to the speech processing circuitry within the ISP 40.

Even when the electrode/transducer array 60 is inserted through the round window 18, which may be necessary for some patients, and may be preferred in other patients, it is noted that the balloon compartment 62 of the array 60 is able to perform the same function of the round window. That is, the balloon compartment 62 sets up fluid vibrations inside of the cochlea as a function of mechanical vibrations that pass through the middle ear.

The speech processing circuitry within the ISP 40 processes the sound signals sensed through the balloon cavity 62 and acoustic transducer 28 and generates control signals therefrom as a function of a particular speech processing strategy. Those control signals derived from the higher frequency sound waves are applied as current stimulation pulses (having a prescribed amplitude, rate, and pulse width) to the electrode contacts 64 of the electrode/transducer array 60, by way of the pulse generation circuitry within the ICS 20, in accordance with the desired speech processing strategy. These current stimulation pulses, in turn, stimulate the ganglion cells in the region of the cochlea where the electrode contacts 64 are located, thereby providing the user with the perception of higher frequency sound. The perception of lower-to-middle frequency sound may occur through normal processes, i.e., activation of functioning hair cells by the fluid waves established within the cochlea through a functioning middle ear chain and round window or balloon compartment membrane. For those patients who also have difficulty sensing lower-o-middle frequency sound, e.g., due to bad or diseased hair cells throughout the cochlea, a longer electrode/transducer array 60 may be employed and inserted deep into the cochlea, as is known in the cochlear stimulation art. In this manner, using the balloon compartment 62 and acoustic transducer 28 as a microphone, a user is able to sense a full range of sounds, from low frequencies to high frequencies.

As seen in FIG. 1, the preferred electrode/transducer array 60 has a length L of about 6–10 mm and a diameter D of about 2 mm. It is made of biocompatible materials using processes and techniques known to those of skill in the implantable electrode art. It includes a shoulder or collar 63 at is proximal end which functions as a stop when the array is inserted through the cochleostomy to the proper depth within the scala tympani 16 of the cochlea 12, and which further functions to seal the cochleostomy so that the cochlear fluids do not escape from the cochlea.

Figures 2, 2A:
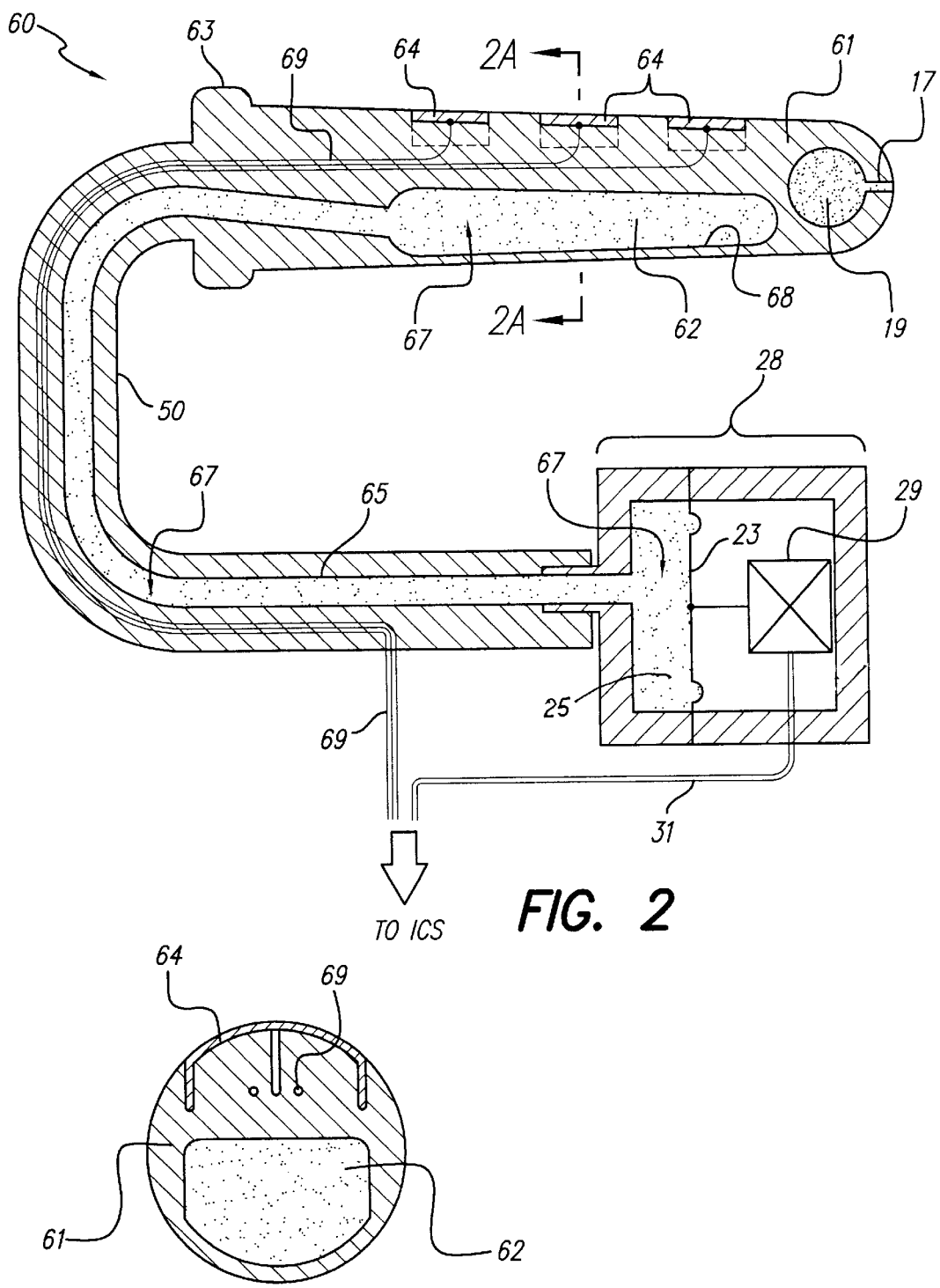
FIG. 2 is a side sectional view of the electrode/transducer provided by the invention, including a functional representation of the acoustic transducer and acoustic modulator, which are in fluid communication with each other.
FIG. 2A is a sectional view of the electrode/transducer taken along the line 2A—2A of FIG. 2.

Turning next to FIGS. 2 and 2A, a more detailed view of the electrode/transducer array 60, and its accompanying acoustic transducer 28, is illustrated. FIG. 2 shows a side sectional view of the electrode/transducer array 60, and FIG. 2A shows a cross-sectional view of the electrode/transducer 60 taken along the line 2A—2A of FIG. 2. As seen in FIG. 2, the main body 61 of the electrode/transducer 60 is made from a suitable flexible biocompatible material, such as a silicone polymer or rubber known as LSR-70 or LSR-25. The properties of LSR-70 and LSR-25are well known in the art, and LSR-70 and LSR-25may be obtained commercially from numerous sources. Such a silicone polymer is also sometimes referred to as"silastic". LSR-70 is formed into a desired shape by injecting or otherwise inserting it into a mold while in a liquid state and allowing it to cure in the mold at a specified temperature for a specified time period. For example, LSR-70 may cure at a temperature of 140 degrees C. for about 15 minutes. LSR-25may likewise be formed into a desired shape using a similar molding process, or it may be applied through a suitable applicator, e.g., a syringe, to a desired area and then formed into a desired shape. LSR-25is essentially the same as LSR-70 except that when it cures it is significantly softer, i.e., more pliable.

The electrode contacts 64 are embedded within the body 61 of the electrode/transducer array 60 so that an exposed surface of each electrode contact remains along one surface of the array body. Preferably, all of the electrode contacts 64 face in the same direction so that when the array 60 is inserted into the cochlea, these electrode contacts may all face the modiolar wall of the cochlea, where the ganglion cells are located. A wire 69 is attached to each electrode contact 64, and each of these wires 69 is embedded within the body 61 of the array, as well as within the flexible lead 50, and are electrically connected to electrical circuitry within the ICS 20 at the other end of the lead 50.

A steroid compartment 19 may be formed within a distal tip of the array 60. Such compartment has an exit channel 17 through which desired drugs or steroids, cached within the compartment 19, may be slowly released over time, e.g., over several days, weeks, months, or years, to the tissue surrounding the array 60. Such drugs or steroids are typically used to to inhibit growth of fibrous tissue or bone tissue, to promote healing, to prevent neural degeneration, and/or to promote neural regeneration, or to otherwise treat the tissue in the vicinity of the array in order to achieve desired therapeutic results. Representative drugs, steroids, or other compounds that may be used within the compartment 19 in accordance with this aspect of the invention include selected steroids, either naturally occurring or synthetic, or a Neuro-trophin selected to prevent neural degeneration and/or to promote neural regeneration.

Still with reference to FIG. 2, the balloon compartment 62 is formed in the body 61 of the array 60 so as to reside on a side of the array opposite the electrode contacts 64. A thin wall 68 separates the balloon compartment 62 from the surface of the array 60. A tunnel (or lumen) 65 fluidly connects the balloon compartment 62 with an acoustic compartment 25 located in the acoustic transducer 28. One wall of the acoustic compartment 25 comprises an hermetic diaphragm 23 mechanically coupled to a transducer element 29, e.g., a piezoelectric crystal. Wires 31 connect the transducer element 29 with other electrical circuitry within the ICS 20. The transducer element 29 converts mechanical motion of the diaphragm 23 to electrical signals, and electrical signals to mechanical motion of the diaphragm 23. Hence, application of appropriate electrical signals to the wires 31 cause the diaphragm 23 to vibrate. Similarly, vibration of the diaphragm 23 causes electrical signals to be generated that are sensed through the wires 31.

A suitable transferring medium 67, e.g., a saline solution, fills the balloon compartment 62, the tunnel 65, and the acoustic compartment 25. Hence, when the balloon compartment 62 of the array 60 is used as a microphone, any fluctuations or movement of the thin wall 68 of the balloon compartment 62 are transferred through the medium 67 to the acoustic compartment 25, causing the diaphragm 23 to vibrate. In turn, vibration of the diaphragm 23 causes electrical signals to be generated that may be sensed through the wires 31. When the transducer portion of the array 60 is used to impart fluid vibrations inside the cochlea, electrical signals applied to the wires 31 cause the diaphragm 23 to vibrate, which vibrations are coupled through the medium 67 to the balloon compartment 62, causing the thin balloon wall 68 to vibrate. Such vibrations of the thin wall 68 are then, in turn, coupled to the fluid within the cochlea.

Advantageously, both LSR-70 and LSR-25, the materials from which the body 61 of the array 60 are preferably made, readily adhere to silastic or silicone tubing so that when cured they become integral therewith. Hence, the electrode/transducer array 60, including the lead 50, having a tunnel 65 passing therethrough, and further including the electrode contacts 64 with wires 69 attached thereto, may readily be fabricated by molding LSR-70 and/or LSR-25. or similar materials, over and around a wiring network comprising the wires 69 and electrode contacts 64 and a silastic tube, the tube having a lumen therethrough which functions as the tunnel 65. Such a molding process may be facilitated through the use of a suitable molding fixture. In such a fixture, the silastic tube with tunnel 65, electrode contacts 64, wires 69, balloon compartment 62, and steroid compartment 19 are all positioned or defined in their respective desired locations. The molding fixture is then filled with LSR-70 and/or LSR-25 or other suitable material while in a liquid state, and the material is allowed to cure, thereby forming the electrode/transducer 60.

Figure 3:
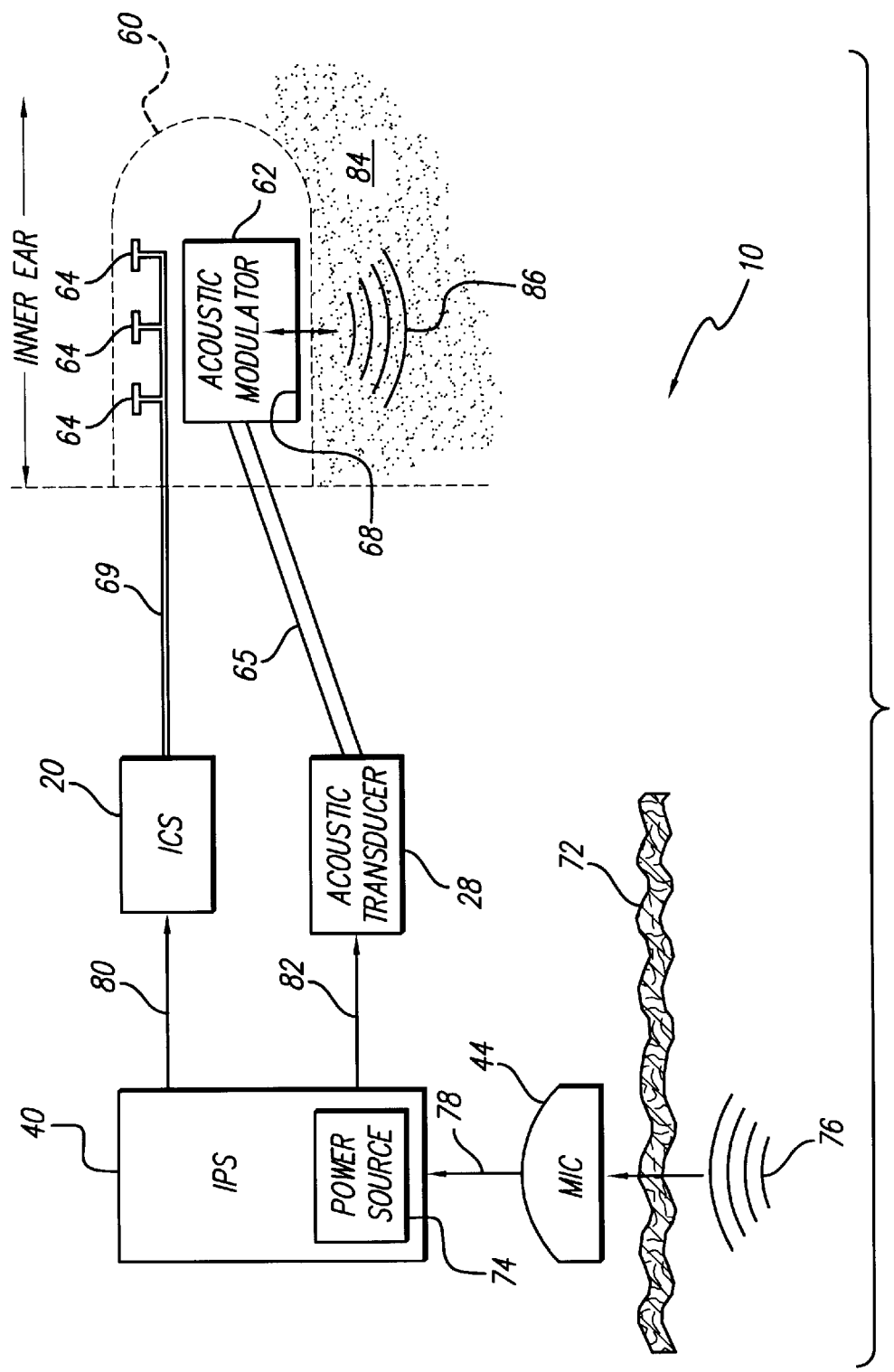
FIG. 3 is a functional block diagram that illustrates operation of the hearing system provided by the invention.

Next, with reference to the functional block diagram of FIG. 3, operation of the hearing system 10 will be illustrated. As seen in FIG. 3, all components of the system 10 are implanted, i.e., located beneath the skin layer 72 of the user of the system. As seen in FIG. 3, the system 10 includes an electrode/transducer array 60 that is adapted for insertion into the basal region of the scala tympani of a human cochlea, i.e., inside the inner ear. The electrode/transducer array 60 has a plurality of spaced-apart electrode contacts 64 thereon, as well as an acoustic modulator 62 therein. The system 10 further includes an implantable cochlear stimulator (ICS) 20 that is electrically coupled to the plurality of electrode contacts 64, and an acoustic transducer (28) that is fluidly coupled to the acoustic modulator 62 by way of a fluid communication channel 65. The system 10 additionally includes an implantable speech processor (ISP) 40 that is electrically coupled to the ICS 20 and the acoustic transducer 28. A power source 74 is housed within the ISP 40, and is operatively coupled to power electrical circuits housed within both the ISP 40 and ICS 20. A microphone 44 is electrically connected to the ISP 40 and is positioned near the skin layer 72 so as to be able to sense incoming acoustic sound waves 76. Such sound waves 76 are converted to electrical signals, which are presented on signal line 78 as an input signal to the ISP 40.

The ISP 40 includes processing circuitry responsive to the electrical signals produced by the microphone. As a result of such processing, at least two sets of control signals are generated. A first set of control signals, provided to the ICS on signal line 80, is representative of high frequency information contained within the acoustic sound waves 76 sensed by the microphone 44. A second set of control signals, provided to the ICS on signal line 82, is representative of lower frequency information contained within the acoustic sound waves 76 sensed by the microphone 44. The processing circuits of the ISP 30 define the first set of control signals as a function of a particular speech processing strategy. Numerous different types of speech processing strategies may be employed by the ISP, as taught, e.g., in U.S. Patent application Ser. No 09/322,712, filed May 28, 1999, incorporated herein by reference.

The ICS 20 includes pulse generating circuitry that, in response to the first set of control signals received on signal line 80, generates electrical stimulation pulses as defined by the first set of control signals and the selected speech processing strategy. These electrical stimulation pulses are applied to the plurality of spaced-apart electrode contacts 64 over wires 69. As a result of such stimulation, electrical stimulation of ganglion cells near the basal end of the cochlea occurs. It is these ganglion cells that are primarily responsible for perception of high frequency information contained within the acoustic sound waves 76 sensed by the microphone 44.

The second set of control signals generated by the ISP 40 is applied to the acoustic transducer 28 over signal line 82. This second set of control signals may comprise simply a digital representation of the lower frequencies present in the incoming acoustic wave 76. Such second set of control signals are used to modulate the acoustic transducer 28. As the acoustic transducer 28 is modulated, such modulation is coupled to the acoustic modulator 62 located within the electrode/transducer array 60 through the fluid communication channel 65. The volume of acoustic modulator 62 varies, typically through movement or flexing of wall 68, as a function of the modulation supplied by the second set of control signals. The variation in the volume of the acoustic modulator 62, in turn, is coupled to fluid 84 within the cochlea, e.g., within the scala tympani, thereby establishing acoustic modulation waves 86 within the cochlear fluid 84. Such acoustic modulation waves 86 correspond to lower frequency information contained within the acoustic sound waves 76 sensed by the microphone 44. These acoustic modulation waves 86, established within the cochlear fluid 84 by the acoustic modulator 62, may then be sensed by functioning hair cells within the cochlea as occurs during the normal hearing process.

An important aspect of the invention relates to its ability to suppress tinnitus. Tinnitus suppression is carried out by generating appropriate pulse sequences in the ICS 20 and then delivering these pulse sequences to selected electrodes 64 on the electrode/transducer array 60. Such suppression may occur at the same time that acoustic enhancement takes place for the lower frequencies through the acoustic modulator 62.

The various components of the invention, i.e., high frequency neural stimulation (through electrode contacts 64), augmented lower frequency hearing (through the acoustic modulator 62), high frequency neural stimulation with signal enhancement (provided through the ISP), lower frequency acoustic signal enhancement (also provided through the ISP), and tinnitus suppression, may advantageously be combined in various ways to address several different applications. (In this context, it is noted that "signal enhancement" means appropriate signal processing, such as amplification, balancing, filtering, phase compensating, smoothing, and the like.) For example, the invention may be used for any or all of the following applications:

(a) high frequency neural stimulation combined with residual lower frequency hearing;
 (b) high frequency neural stimulation signal enhancement combined with lower frequency acoustic signal enhancement;
 (c) tinnitus suppression;
 (d) tinnitus suppression combined with acoustic signal enhancement;
 (e) higher frequency neural stimulation signal enhancement, acoustic signal enhancement, and tinnitus suppression stimulation; or
 (f) tinnitus suppression combined with cochlear neural stimulation.

As described above, it is thus seen that the present invention provides a versatile fully implantable hearing system that may restore hearing function over a wide frequency band, e.g., from low frequencies to high frequencies.

As described above, it is additionally seen that the invention provides a versatile system that can be used for a wide variety of applications, ranging from higher frequency neural stimulation, with or without signal enhancement (balancing, smoothing and phase compensation); tinnitus suppression; residual lower frequency hearing, or lower frequency acoustic signal enhancement.

As further described above, it is also seen that one embodiment of the invention provides a implantable cochlear microphone able to sense acoustic signals inside of the cochlea that pass through a functioning middle ear or other path.

While the invention herein disclosed has been described by means of specific embodiments and applications thereof, numerous modifications and variations could be made thereto by those skilled in the art without departing from the scope of the invention set forth in the claims.

What is claimed is:

1. An implantable hearing system (10) comprising:
 an electrode/transducer array (60) adapted for insertion into the basal region of the scala tympani of a human cochlea, the electrode/transducer array having a plurality of spaced-apart electrode contacts (64) thereon, and an acoustic modulator (62) therein;
 an implantable cochlear stimulator (ICS) (20) electrically coupled to the plurality of electrode contacts;
 an acoustic transducer fluidly coupled to the acoustic modulator of the electrode/transducer array;
 an implantable speech processor (ISP) (40) electrically coupled to the ICS and acoustic transducer;
 a power source operatively coupled to the ICS and ISP;
 a microphone connected to the ISP, wherein the microphone senses acoustic sound and converts such sensed acoustic sound to electrical signals; and
 processing circuitry within the ISP responsive to the electrical signals produced by the microphone, the processing circuitry including means for generating a first set of control signals representative of high frequency information contained within the acoustic sound sensed by the microphone, and for generating a second set of control signals representative of lower frequency information contained within the acoustic sound sensed by the microphone; and further
 wherein the ICS includes pulse generating circuitry that generates electrical stimulation pulses as defined by the first set of control signals generated by the ISP, and further wherein the electrical stimulation pulses are applied to the plurality of spaced-apart electrode contacts in a prescribed manner, whereby electrical stimulation of the cochlea is provided corresponding to high frequency information contained within the acoustic sound sensed by the microphone; and additionally
 wherein the second set of control signals are applied to and modulate the acoustic transducer, wherein the fluid coupling with the acoustic modulator causes the volume of the acoustic modulator to vary as a function of the modulation supplied by the second set of control signals, and wherein variations in the volume of the acoustic modulator of the electrode/transducer array are adapted to be coupled to fluid within the scala tympani, whereby acoustic modulation of the fluid within the scala tympani is provided corresponding to lower frequency information contained within the acoustic sound sensed by the microphone.

2. The implantable hearing system of claim 1 wherein said acoustic modulator comprises a balloon compartment having a thin wall formed within the electrode/transducer array, and wherein the balloon compartment is in fluid communication with the acoustic transducer.

3. The implantable hearing system of claim 1 wherein the acoustic transducer comprises an electrical-to-mechanical transducer (29) mechanically coupled to a moveable diaphragm (23), wherein the moveable diaphragm comprises a wall of a fluid compartment (25), wherein a transferring medium (67) is stored, and further wherein the fluid compartment (25) is in fluid communication by way of a tunnel (65) with the acoustic modulator (62).

4. The implantable hearing system of claim 3 wherein the acoustic modulator (62) and acoustic transducer function as a microphone, wherein the acoustic modulator senses fluid waves within the cochlea, and the acoustic transducer converts such sensed fluid waves to an electrical signal.

5. The implantable hearing system of claim 1 wherein the electrode/transducer array further includes a storage compartment (19) formed therein in which a desired drug may be stored and slowly released for the purpose of achieving a desired therapeutic effect, such as inhibition of tissue or bone growth in the vicinity of the electrode/transducer array..

6. The implantable hearing system of claim 1 wherein the power source comprises a rechargeable battery housed within the ISP.

7. The implantable hearing system of claim 6 wherein the ICS includes a coil (24) attached thereto through which programming and recharging signals may be received.

8. The implantable hearing system of claim 1 wherein the electrode/transducer array (60) comprises a carrier body (61) made from a silicone polymer, such as LSR-70 or LSR-25, on which the spaced-apart electrode contacts are carried, and inside of which the acoustic modulator is housed.

9. The implantable hearing system of claim 8 wherein the carrier body has a length of between about 6 to 10 mm, and a diameter of approximately 2 mm.

10. The implantable hearing system of claim 1 wherein the ISP (40) is electrically connected to the ICS (20) by way of a detachable cable (30).

11. An implantable hearing system comprising:

an electrode/transducer array adapted for insertion into a human cochlea, wherein the electrode/transducer array has a plurality of spaced-apart electrode contacts carried thereon, and wherein the electrode/transducer array further has an acoustic modulator carried therein;

an acoustic transducer in fluid communication with the acoustic modulator by way of a fluid communication channel, wherein the acoustic transducer includes an electrical-to-mechanical transducer coupled to a fluid chamber, wherein the fluid chamber has at least one movable or flexible wall, and wherein the fluid chamber is in fluid communication with the fluid communication channel, and further wherein the electrical-to-mechanical transducer is attached to the flexible wall of the fluid chamber;

an implantable cochlear stimulator (ICS) in electrical communication with the plurality of spaced-apart electrode contacts of the electrode/transducer array by way of a bundle of wires;

wherein the fluid communication channel and the bundle of wires are carried within a flexible lead;

an implantable speech processor (ISP) in electrical communication with the ICS and the acoustic transducer; and an implantable microphone coupled to the ISP;

wherein the ISP includes processing circuitry that processes sound waves sensed by the implantable microphone and generates control signals as a function thereof; and wherein the ICS includes pulse generating circuitry for generating electrical stimulation pulses having an amplitude, rate, and pulse width controlled by the control signals;

wherein the electrical stimulation pulses are applied to the electrode contacts in accordance with a prescribed speech processing strategy.

12. The implantable hearing system of claim 11 wherein the microphone comprises the acoustic modulator, the acoustic transducer, and the fluid communications channel; wherein the acoustic modulator senses fluid modulation occurring within the cochlea, transfers the sensed fluid modulation by way of the fluid communications channel to the acoustic transducer, and the acoustic transducer converts the sensed fluid modulation to an electrical signal.

13. The implantable hearing system of claim 11 wherein the microphone comprises a movable diaphragm coupled to a mechanical-to-electrical transducer, and wherein the movable diaphragm is formed within a wall of the ISP.

14. The implantable hearing system of claim 11 wherein speech processing circuitry within the ISP modulates the acoustic transducer with selected frequency components of an acoustic signal sensed through the microphone, and further wherein the modulation applied to the acoustic transducer is coupled through the fluid communication channel to the acoustic modulator, and wherein the acoustic modulator transfers the modulation to fluid within the cochlea.

15. An electrode array adapted for insertion into the cochlea comprising:

a non-conductive carrier body (61);

a plurality of spaced-apart electrode contacts (64) carried on the carrier body, each electrode contact having a wire (69) connected thereto through which electrical connection with the respective electrode contacts may be established;

an acoustic modulator (62) formed within the carrier body; and a tunnel (65) passing through the carrier body that is in fluid communication with the acoustic modulator; and a flexible lead integrally attached to the carrier body, wherein the wire attached to each electrode contact, and the acoustic modular and the tunnel channel are embedded within said flexible lead.

16. The electrode array of claim 15 wherein the carrier body has a length of from 6–10 mm, and a diameter of about 2 mm.

17. The electrode array of claim 15 wherein the number of electrode contacts (64) included on the array is no more than five.

18. The electrode array of claim 17 wherein the number of electrode contacts included on the array is three.

* * * * *